(12) United States Patent
Woo et al.

(10) Patent No.: US 7,220,372 B2
(45) Date of Patent: May 22, 2007

(54) DUAL DENSITY EARPLUG

(75) Inventors: Ed win Woo, Chula Vista, CA (US); John Allen Jenkins, Jr., San Diego, CA (US)

(73) Assignee: Howard Leight Industries, LLC, San Diego, CA (US)

( * ) Notice: Subject to any disclaimer, the term of this patent is extended or adjusted under 35 U.S.C. 154(b) by 180 days.

(21) Appl. No.: 11/000,649

(22) Filed: Dec. 1, 2004

(65) Prior Publication Data

US 2006/0118124 A1 Jun. 8, 2006

(51) Int. Cl.
*B29C 44/06* (2006.01)
*B29C 44/12* (2006.01)

(52) U.S. Cl. .................. 264/46.7; 264/46.4; 264/46.6; 264/255; 264/267

(58) Field of Classification Search ............... 264/46.4, 264/255, 267, 46.6, 46.7
See application file for complete search history.

(56) References Cited

U.S. PATENT DOCUMENTS

| | | | |
|---|---|---|---|
| 4,434,794 A | 3/1984 | Leight | |
| 5,188,123 A | 2/1993 | Gardner, Jr. | |
| 5,573,015 A | 11/1996 | Williams | |
| 2002/0124851 A1 | 9/2002 | Knauer et al. | |
| 2005/0039761 A1* | 2/2005 | Jenkins, Jr. | 128/864 |

* cited by examiner

*Primary Examiner*—Allan R. Kuhns
(74) *Attorney, Agent, or Firm*—Leon D. Rosen

(57) ABSTRACT

An earplug (10) that includes a soft foam body (12) and a stiffener (14) in the body, is produced by a method that has minimum steps and that results in an earplug of attractive design and that uses a minimum of material. One method includes molding an earplug body in a body cavity (52) while a mandrel (56) lies in the body cavity. After the foam material in the body cavity has at least partially solidified, the mandrel is removed, leaving an empty stiffener cavity (60) in the foam body (12). With the body remaining in the body mold (54), flowable stiffener material (14A) is poured into the stiffener cavity of the body and allowed to solidify, to produce an earplug with a molded-in stiffener (14). Another method, results in an earplug (90) with a stem (95) having a rearwardly-projecting stem portion (96). This method includes molding a stem rear portion (96) in a stiffener cavity (110) while allowing stiffener material to project forward of the rear portion to form a stem free front portion (120). The free front portion is projected into a body cavity (104) while foam material in the body cavity is still plastically deformable.

10 Claims, 2 Drawing Sheets

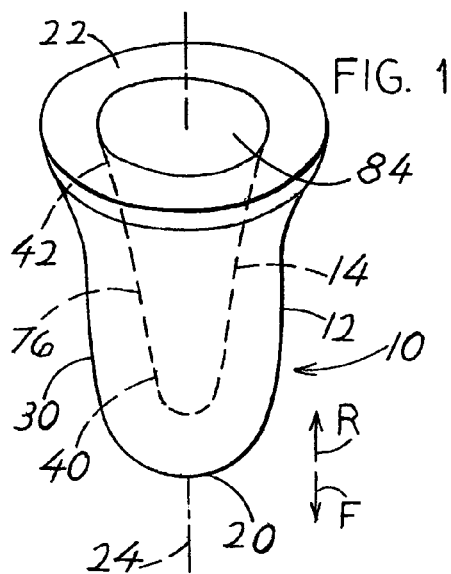
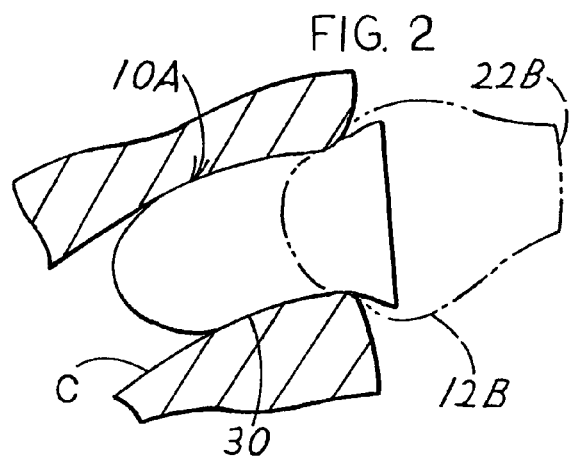
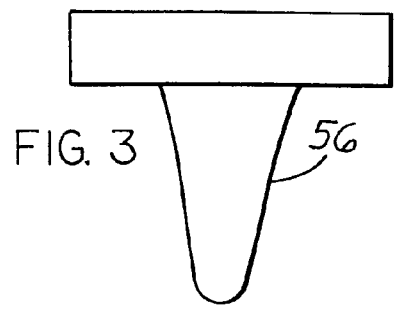
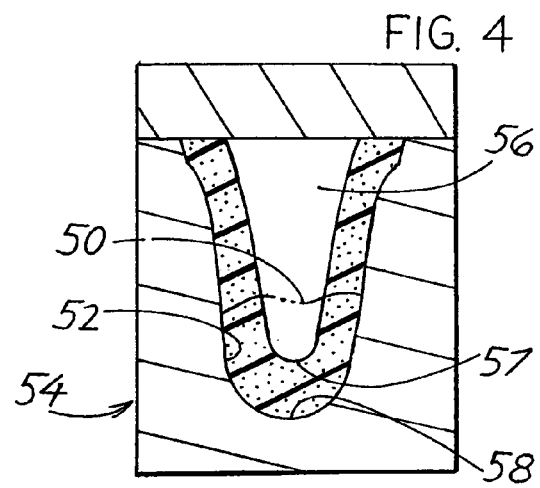
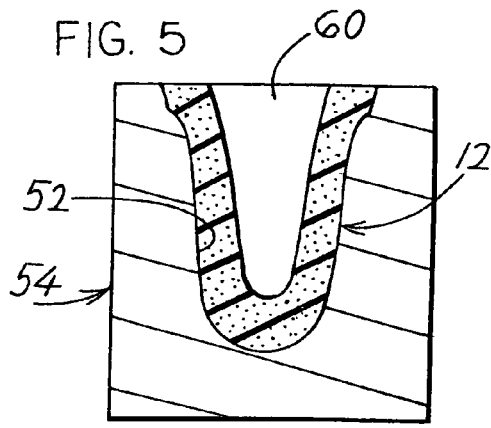
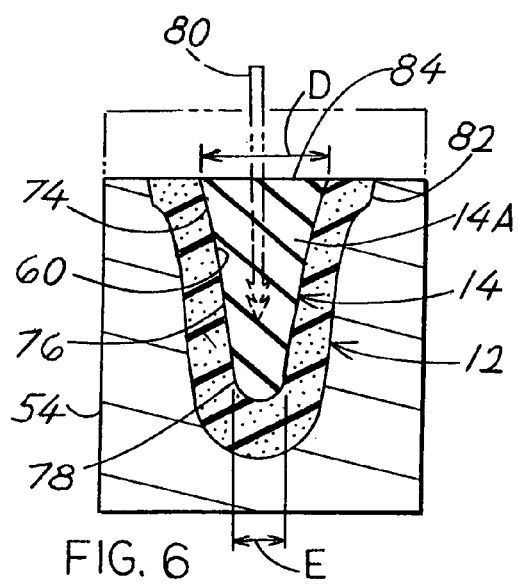

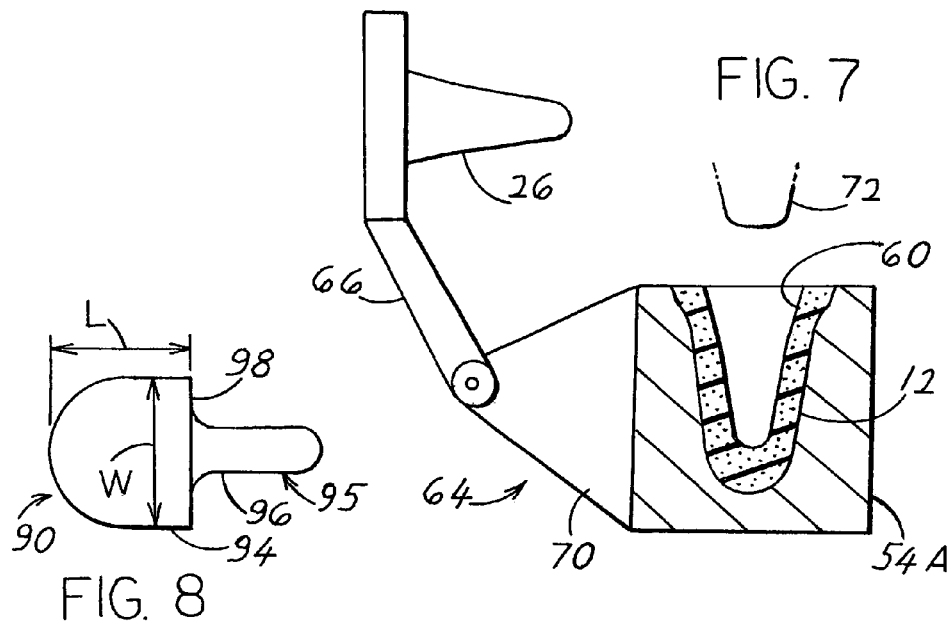
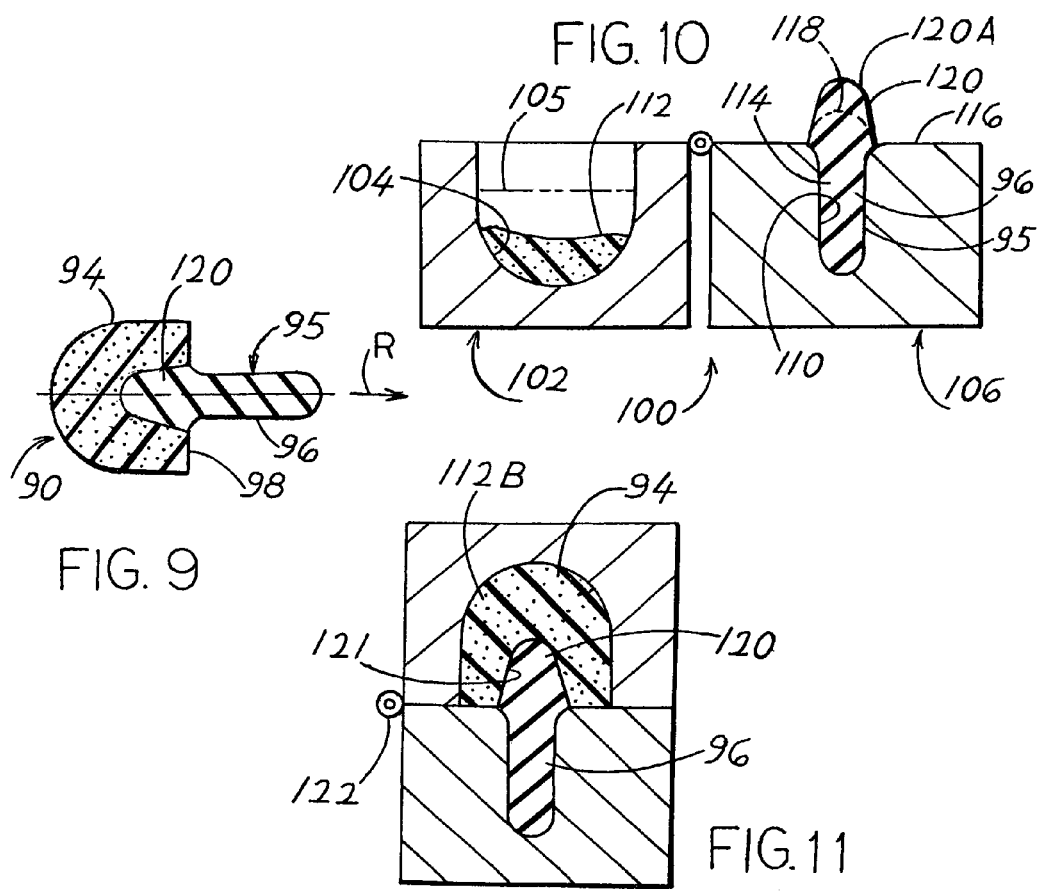

DUAL DENSITY EARPLUG

BACKGROUND OF THE INVENTION

One type of earplug includes a soft foam body that is to be inserted into a person's ear canal to block noise. To help push the soft foam body into the ear canal, a stiffener of material stiffer than that of the foam body, is placed in the body. One way to place the stiffener in the body is to mold the body around the stiffener. U.S. Pat. No. 5,573,015 by Williams forms a long rod of stiffener material and passes it though an extrusion head while foam material is extruded around the rod and the resulting extrusion is cut into earplugs. This has the disadvantage that the rod front end lies at the front end of the earplug, resulting in a concern of people that the rod will scrape against the ear canal during insertion therein. Also, the stiffener rod is of uniform diameter and cannot produce the desired stiffness during insertion combined with flexibility to bend.

One type of earplug with stiffener, shown in U.S. Pat. Nos. 5,188,123 and 4,774,938, includes a largely hemispherical earplug body and a thin rod with a front end embedded deeply in the body. All of the hemispherical body is inserted into the ear canal, and it requires little foam material. The rod front end forms a stiffener, and the rod rear end forms a handle that can be grasped to push in and pull out the body from the ear canal. There is a possibility that the rod will separate from the body and leave the body in the ear canal. It would be desirable if the exposed rod rear end were molded for attractive shape, and the rod front end were molded intimately into the body to assure very good bonding of the rod to the body.

SUMMARY OF THE INVENTION

In accordance with the invention, applicant provides molding methods and corresponding earplugs, wherein the earplugs have stiffeners that are molded intimately into soft foam bodies in methods that involve a minimum of handling. One method includes molding the earplug body in a body mold cavity, while a mandrel lies in the cavity with the mandrel front end spaced from the body cavity front end. The mandrel forms a stiffener cavity in the molded foam body. After the foam body solidifies at least partially, the mandrel is removed while the body remains in the body cavity, and stiffener material is poured into the stiffener cavity left by the mandrel. The resulting earplug has a stiffener molded into the body. The stiffener can have a highly tapered shape to provide the required stiffness for earplug insertion, but allow the earplug to bend to follow the curvature of a person's ear canal. The method requires a minimum number of steps in molding and handling the earplug parts.

Another method, which produces a small earplug body with rearwardly projecting stem, includes placing foamable material in a body cavity of a body mold, and placing stiffener material in a stiffener cavity of a stiffener mold. Stiffener material not only fills the stiffener cavity, but projects forward of the front end of the stiffener mold, to leave a stiffener free front end that is not surrounded by stiffener mold walls. The molds are moved together so the stiffener free front end is projected into the body cavity that holds foamable material that still can be plastically deformed, to embed the stiffener free front end in the body. This method also involves minimum handling of parts.

The novel features of the invention are set forth with particularity in the appended claims. The invention will be best understood from the following description when read in conjunction with the accompanying drawings.

BRIEF DESCRIPTION OF THE DRAWINGS

FIG. 1 is a rear and side isometric view of an earplug of one embodiment of the present invention, with the stiffener portion that is embedded in the earplug body being shown in hidden lines.

FIG. 2 is a side view of a curved ear canal, showing the earplug of FIG. 1 fully inserted therein, and showing in phantom lines, an earplug solely of foam during an attempt to insert it.

FIG. 3 is a side elevation of a mandrel that is part of an earplug mold that produces the earplug of FIG. 1.

FIG. 4 is a sectional view of an earplug mold showing the mandrel of FIG. 3 lying in a body mold, and with foamable material in the body mold cavity.

FIG. 5 is a sectional view of the mold of FIG. 4, with the mandrel removed to leave a stiffener cavity in the earplug body.

FIG. 6 is a sectional view of the mold of FIG. 5, with stiffener material lying in the stiffener body, and also showing a sectional view of the final earplug of FIG. 1.

FIG. 7 is a partially sectional side elevation view of an apparatus for holding the body mold and the mandrel of FIG. 3-6, to produce an earplug using a minimum of steps.

FIG. 8 is a side elevation view of a stem earplug, of another embodiment of the present invention.

FIG. 9 is a sectional view of the earplug of FIG. 8.

FIG. 10 is a sectional view of apparatus for use in forming the earplug of FIG. 9, with foamable material in the body mold and with a stiffener molded in and above the stiffener mold.

FIG. 11 is a sectional view of the apparatus shown in FIG. 10, with the body and stiffener molds moved together to form the earplug of FIG. 9.

DESCRIPTION OF THE PREFERRED EMBODIMENTS

FIG. 1 illustrates an earplug 10 of one embodiment of the invention, which includes a body 12 formed of a soft and resilient foam and a stiffener 14 formed of an elastomeric material that is more than twice as stiff as the soft foam material of the body. The earplug has front and rear ends 20, 22 spaced apart in front F and rear R directions along the axis 24 of the earplug. A sealing part 30 serves to seal to a person's ear canal. FIG. 2 shows the sealing part 30 of an earplug at 10A lying in an ear canal C. Without the stiffener, it is likely that an earplug body 12B with the rear end 22B pushed forward, would undergo column collapse and bulge as shown at 12B and not enter the ear canal.

Applicant notes that the ear canal C is curved, and that the earplug bends to follow the curvature. The stiffener 14 of FIG. 1 is tapered in diameter, with its middle 76 and front portion 40 of smaller diameter than its rear portion 42. This results in a stiffener front portion that is thinner and that can more easily bend. It also results in a thicker stiffener rear portion that is more resistant to any bending or collapse, so it can help the earplug sealing portion be inserted into the ear canal.

FIG. 4 shows a first step in forming the earplug 10 of FIG. 1. A quantity 50 of foamable material that will increase in volume as it foams and will solidify to become a soft foam, is deposited in a body cavity 52 of a body mold 54. Before the foam has solidified, a mandrel 56 is placed in the body cavity as shown in FIG. 4, with a front end 57 of the mandrel spaced from a front end 58 of the body cavity. The mandrel 56 has the shape shown in FIG. 3. After the soft foam material has largely solidified, the mandrel is removed from the body cavity. The body then has the construction shown in FIG. 5, with an empty stiffener cavity 60 inside the molded body 12, and with the body still lying in the cavity 52 of the body mold 54.

A next step, shown in FIG. 6, is to pour, or deposit, a quantity 14A of flowable stiffener material in the stiffener cavity 60. When the stiffener material solidifies, it becomes the stiffener 14 of the earplug. The withdrawal of the mandrel 26 in FIGS. 4 and 5 and the molding of the stiffener in FIG. 6 all occur while the molded body 12 continues to remain in the body mold 54. This reduces the number of times the body is handled and the number of steps required to mold the earplug, and therefore reduces the cost. After the stiffener is molded, the earplug is ejected from the body mold.

FIG. 7 illustrates one possible apparatus 64 which is useful to perform the steps of FIGS. 4 though 6. In the apparatus, the mandrel holder 66 is pivotally mounted on an extension 70 of the body mold 54A. This allows the mandrel to be easily and accurately moved between its positions in and out of the body mold. The figure also shows one of two moveable dispenser heads 72 that can dispense the proper amounts of foamable material and stiffener material in the body cavity and stiffener cavity.

One example of the material of the earplug is a soft foam for the body having a stiffness of one to five on the Shore A scale, and a stiffener material that is elastomeric (i.e. having a Young's Modulus of Elasticity of no more than 50,000 psi) and that has a stiffness of twenty on the Shore A scale. The stiffness of the stiffener material varies with the diameter of the stiffener, with a lower stiffness desirable when a larger diameter stiffener is used. Applicant prefers to use a stiffener with a rear part 74 (FIG. 6) having a diameter D at least 150%, and preferably at least 200% of the diameter E of the front part (before the front part is rounded, if it is rounded). The wide rear end helps prevent collapse during earplug insertion, while the narrower middle 76 and front end 78 allow the earplug to bend to follow a curved ear canal and facilitate earplug body compression by the ear canal.

FIG. 6 shows, in phantom lines, the possibility of placing a post 80 in the stiffener to help insert and remove the earplug from the ear canal. However, the rear flange 82 of the earplug is sufficient for removal, and pressing the finger against the rear end 84 of the stiffener is usually the easiest way to insert the earplug into the ear canal.

FIGS. 8 and 9 show another earplug 90 which is of the type that includes a rod, or stem 95 that has a front stiffener portion at 120 lying in an earplug body 94, and a rear handle portion 96 that projects at least one centimeter rearward R of the body. The earplug body is of generally hemispherical shape, with a rounded front end and a largely flat rear end 98. The body is of short length L compared to its diameter or width W, with the length L preferably being no more than 125%, and preferably no more than 110% of the width. This allows the entire body to be inserted into the ear canal, and allows the saving of material that is used to make the body. Earplugs may sell in large quantities for a price of perhaps five cents each, and minimizing the amount of material is desirable. It is also desirable to minimize the number of steps and to use simple steps, to manufacture the earplug, and to produce an earplug with an appearance that indicates it is of high quality.

FIG. 10 illustrates early steps in the manufacture of the earplug of FIGS. 8 and 9. The manufacturing apparatus 100 includes a body mold 102 with a body cavity 104, and a rod or stem mold 106 with a stem cavity 110. A quantity 114 of liquid or otherwise flowable stiffener material such as rubber is deposited in the stem cavity 110. A sufficient quantity of stem material is deposited in the stem cavity to create a slight overflow at 118 above the top 116 of the stem mold. This creates a lower part of a stem front portion 120 that will be embedded in the body. To increase the height of the free stem portion 120A which is not surrounded by mold walls, applicant can drip some flowable stem material on top of the overflow 118 of the free stem portion while the already deposited material begins to solidify sufficiently, that the newly deposited material primarily increases the height of the free stem portion while minimizing increase in its width. It is also possible to place a wrap around the free stem portion to shape it and remove the wrap when the free stem portion has partially solidified. When the free stem portion solidifies into the front stem portion 120, the front stem portion preferably is longer than its average width.

A quantity 112 of foamable soft foam material is deposited in the body cavity 104. At some time during the foaming and solidification of the foam material, as when the foam has reached the height 105, the two molds are brought together as shown in FIG. 11. FIG. 11 shows a pivot joint 122 connecting the molds. The foam material 112B in FIG. 11 is sufficiently plastically (permanently deformable) while the stem front portion 120 is sufficiently solidified, that the stem front portion penetrates into the foam material or limits its foaming to an area around the stem front portion. When the foam material fully solidifies it becomes the earplug body 94. The result is an earplug of the type shown in FIG. 9, wherein the stem front portion 120 has penetrated the body sufficiently to assure that the body can be fully inserted into a person's ear canal, and to assure that the stem will remain adhered to the body so it will not pull out of the body and leave the body in the ear canal. To increase the bonding of the stem material to the body material, applicant prefers that the stem material not be completely solidified, as where its temperature is still at least 130° F., when it contacts the not-yet-solidified foam. The fact that the stem front portion was bonded to the body in this way can be determined by microscopic examination of the earplug. The rearward portion 96 of the stem, as well as the body 94, are molded in mold walls, so both of them have even shapes that suggest a high quality product. The stem and body are held in their respective molds until the earplug is completed.

Thus, the invention provides earplug that each includes a soft foam body and a more rigid stiffener or stem, where each earplug can be molded using a minimum of handling of the body and stiffener or stem. In one earplug, the body is molded with a stiffener cavity that is later filled with a stiffener material, and preferable with the stiffener being tapered in diameter. Only then is the body removed from its mold. In another earplug, the stem has a rear portion that projects rearward from a body of small length, and has a front portion that is formed free of mold walls. This allows the stem front portion to be simply projected into the body cavity when the body is not yet fully solidified, while the body lies in its body cavity and the stem rear portion lies in its stem mold cavity.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method for molding earplugs that each includes a body of resilient soft foam material and a stiffener in said body, comprising:

establishing foamable material of said body in a body cavity of a body mold, and allowing the foamable material to expand in the body cavity to form at least a major portion of said body;

establishing a majority of a quantity of flowable but solidifiable elastomeric stiffener material that is more than twice as stiff as said foamable material of said body when both materials solidify, in a stiffener cavity to form at least a major portion of said stiffener in said stiffener cavity, including establishing at least a front portion of the stiffener in said body cavity and allowing said materials of said body and stiffener to solidify and bond to one another, all without removing said body from the body cavity, and without removing said stiffer major portion from said stiffener cavity, whereby to minimize handling of parts.

2. A method for molding earplugs that each includes a body of soft foam material and a stiffener in said body, comprising:

establishing foamable material of said body in a body mold cavity that has an axis, while a mandrel lies in said body mold cavity and is centered on said axis, so the foamable material expands in the earplug cavity to form a body with an inner stiffener cavity where the mandrel lies;

after said foamable material of said body at least partially sets, removing said mandrel to leave said inner stiffener cavity empty, establishing a flowable and solidifiable stiffener material in said inner stiffener cavity, wherein when said stiffener material has solidified it is stiffer than said foam material, and allowing said stiffener material to solidify.

3. The method described in claim 2 including:

said step of establishing a flowable stiffener material in said inner stiffener cavity, includes leaving said body with an inner stiffener cavity in said earplug mold in which said foamable material expanded, while pouring said flowable stiffener material into said inner stiffener cavity.

4. A method for molding earplugs that each includes a body of soft foam material and a stiffener of stiffener material that is stiffer than said soft foam material, said stiffener having a front stiffener portion that lies in said body and a rear stiffener portion that projects rearward of said body and that forms a handle that is graspable during insert of the body in an ear canal and during removal of the body from the ear canal, comprising:

molding a rear portion of the stiffener in a cavity of a first mold, while establishing stiffener material at a front portion of the stiffener that projects out of the cavity and forms a projecting stiffener portion;

holding said soft foam material in a body cavity and, while said soft foam material is in a state wherein it is plastically deformable, moving said first mold and body cavity closer until said front portion of said stiffener lies in a rear portion of said body cavity, and allowing said materials to solidify.

5. A method for molding earplugs that each includes a body of resilient soft foam material and a stiffener in said body, comprising:

establishing foamable material of said body in a body cavity of a body mold, establishing a mandrel in said body cavity with the mandrel centered on a body cavity axis and allowing the foamable material to expand in the body cavity to form at least a major portion of said body with an inner stiffener cavity where the mandrel lies;

removing said mandrel to leave said stiffener cavity empty, and then pouring a quantity of flowable but solidifiable elastomeric stiffener material that is more than twice as stiff as said foamable material of said body when both materials solidify, in said stiffener cavity to form at least a major portion of said stiffener in said stiffener cavity, including establishing at least a front portion of the stiffener in said body cavity and allowing said materials of said body and stiffener to solidify and bond to one another, all without removing said body from the body cavity, and without removing said stiffer major portion from said stiffener cavity, whereby to minimize handling of parts.

6. The method described in claim 5 including:

inserting a front end of a post (80) into said stiffener before it solidifies, with a rear end of the post projecting rearward of the body mold cavity.

7. A method for molding earplugs that each includes a body of resilient soft foam material and a stiffener in said body wherein said stiffener has a rear portion that extends rearward of said body by at least a centimeter to form a handle, comprising:

establishing foamable material of said body in a body cavity of a body mold, and allowing the foamable material to expand in the body cavity to form at least a major portion of said body;

establishing a majority of a quantity of flowable but solidifiable elastomeric stiffener material that is more than twice as stiff as said foamable material of said body when both materials solidify, in a stiffener cavity that is separate from said body mold including forming a front portion of said stiffener so it is free of engagement with walls of said stiffener mold as said front portion of said stiffener is formed;

establishing at least a portion of the stiffener in said body cavity including pressing at least said front stiffener portion into said foamable material while said foamable material still lies in said body cavity, and allowing said materials of said body and stiffener to solidify and bond to one another.

8. The method described in claim 7 wherein:

said step of molding said stiffener includes molding said stiffener rear portion in a stiffener mold cavity while forming said stiffener front portion as a projection that projects forward of said stiffener mold cavity;

said step of pressing at least said front stiffener portion into said body mold cavity, occurs while said stiffener rear portion remains in said stiffener mold cavity to thereby provide an earplug with a molded stem.

9. The method described in claim 7 wherein:

said step of establishing said front projecting stiffener portion in said rear portion of said body cavity, includes pressing said front projecting stiffener portion into said body cavity while said projecting stiffener portion is heated above 130° F., whereby to establish a better bond of the stiffener to the body.

10. The method described in claim 7 wherein:

said step of establishing said front projecting stiffener portion in said rear portion of said body cavity, includes first allowing said foam to expand to fill a majority of its said body cavity, and then establishing said projecting stiffener portion in said body cavity.

* * * * *